United States Patent
Wang

(10) Patent No.: US 10,321,071 B1
(45) Date of Patent: Jun. 11, 2019

(54) WEARABLE DEVICE CAPABLE OF DISPLAYING OBJECT TEMPERATURE

(71) Applicants: LEAPSY International Ltd., New Taipei (TW); Po-Wen Wang, New Taipei (TW)

(72) Inventor: Po-Wen Wang, New Taipei (TW)

(73) Assignees: LEAPSY INTERNATIONAL LTD., New Taipei (TW); Po-Wen Wang, New Taipei (TW)

( * ) Notice: Subject to any disclaimer, the term of this patent is extended or adjusted under 35 U.S.C. 154(b) by 0 days.

(21) Appl. No.: 15/910,016

(22) Filed: Mar. 2, 2018

(30) Foreign Application Priority Data

Dec. 28, 2017 (TW) .................... 106219313

(51) Int. Cl.
*H04N 5/33* (2006.01)
*H04N 5/235* (2006.01)
*H04N 5/225* (2006.01)
*G08C 17/00* (2006.01)
*G06K 9/00* (2006.01)
*G01P 15/00* (2006.01)
*A61B 5/00* (2006.01)
*A61B 5/01* (2006.01)
*A61B 5/113* (2006.01)

(52) U.S. Cl.
CPC ........... *H04N 5/332* (2013.01); *A61B 5/0008* (2013.01); *A61B 5/01* (2013.01); *A61B 5/113* (2013.01); *A61B 5/742* (2013.01); *G01P 15/008* (2013.01); *G06K 9/00671* (2013.01); *G08C 17/00* (2013.01); *H04N 5/2258* (2013.01); *H04N 5/2354* (2013.01); *H04N 5/33* (2013.01); *G08C 2201/93* (2013.01)

(58) Field of Classification Search
CPC ......... A61B 5/0008; A61B 5/01; A61B 5/113; A61B 5/742; G01P 15/008; H04N 5/33; H04N 5/332
See application file for complete search history.

(56) References Cited

U.S. PATENT DOCUMENTS

| 2013/0072763 | A1* | 3/2013 | Shtalryd | A61B 5/01 600/301 |
| 2015/0055886 | A1* | 2/2015 | Oh | G06T 3/4038 382/284 |
| 2015/0146009 | A1* | 5/2015 | Kostrzewa | H04N 5/2256 348/164 |
| 2015/0182114 | A1* | 7/2015 | Wang | A61B 90/96 600/549 |

* cited by examiner

*Primary Examiner* — Shawn S An
(74) *Attorney, Agent, or Firm* — Raymond Y. Chan; David and Raymond Patent Firm

(57) ABSTRACT

A wearable device capable of displaying an object temperature includes a camera, an image capturing unit, a thermal camera, a thermal sensing device, a central processing unit and a display unit. The camera receives light to generate an image, and the image is captured by the image capturing unit. The thermal camera receives light to generate a thermal image. The thermal image is received by the thermal sensing device to obtain temperature information. The captured image and the thermal image are transmitted to the central processing unit and calculated by the central processing unit to obtain a temperature value for each point of the thermal image. The temperature values are displayed on the display unit.

7 Claims, 2 Drawing Sheets

WEARABLE DEVICE CAPABLE OF DISPLAYING OBJECT TEMPERATURE

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The invention relates to a wearable device capable of displaying a temperature of an object.

Description of Related Arts

Conventional temperature measuring devices include typical thermometers, infrared thermometers and thermal lenses. In these devices, the typical thermometer responses very slow and must contacts human's body. The infrared thermometer can measure only a point. The thermal lens can measure a predetermined view angle range.

SUMMARY OF THE PRESENT INVENTION

An object of the invention is to provide a wearable device of displaying a temperature of an object. An image and a thermal image of a real scene are captured, and a basis temperature is preset. The thermal image is calculated to obtain a temperature value for each point of the thermal image. The temperature value exceeding the basis temperature and the image of the real scene are displayed on the display unit.

The invention provides a wearable device capable of displaying a temperature of an object. The wearable device in accordance with an exemplary embodiment of the invention includes a camera configured to receive external light to form an image; an image capturing unit configured to capture the image; a thermal camera configured to receive external light to generate a thermal image; a thermal sensing device configured to receive the thermal image to generate temperature information; a central processing unit configured to receive the image and the thermal image, overlap the image and the thermal image, calculate a value of a temperature for each point in the thermal image and compare the value of the temperature with a basis temperature; and a display unit connected to the central processing unit, wherein the central processing unit transmits the value of the temperature exceeding the basis temperature to the display unit to display the value of the temperature on a position where the temperature occurs.

A temperature of a person or an object is measured and displayed in a real time through the wearable device of the invention. The wearable device and the method of the invention can be applied to quarantine, fire accident preventing or industry.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE PREFERRED EMBODIMENT

The following description is of the best-contemplated mode of carrying out the invention. This description is made for the purpose of illustrating the general principles of the invention and should not be taken in a limiting sense. The scope of the invention is best determined by reference to the appended claims.

Figure 1:
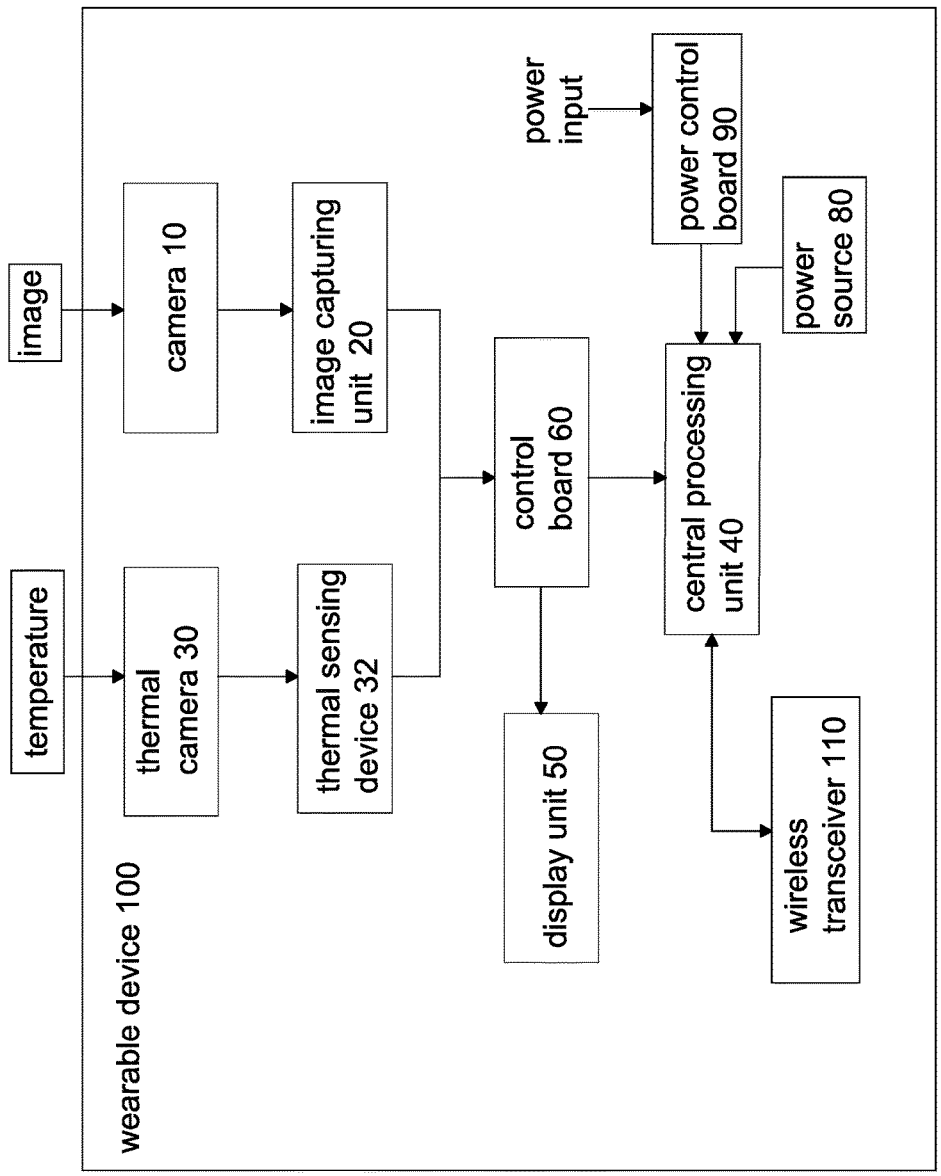
FIG. 1 is a block diagram of an embodiment of a wearable device capable of displaying an object temperature of the invention.

Referring to FIG. 1, a wearable device 100 capable of displaying a temperature of an object of the invention includes a camera 10, an image capturing unit 20, a thermal camera 30, a thermal sensing device 32, a central processing unit 40 and a display unit 50. The camera 10 is configured to receive external light to form an image. The image capturing unit 20 is configured to capture the image. In this embodiment, the image capturing unit 20 is a charge-coupled device (CCD) or complementary metal-oxide-semiconductor (CMOS) photo-sensing element. The central processing unit 40 is configured to receive the image. The thermal camera 30 receives the external light to form a thermal image. The thermal sensing device 32 is configured to receive the thermal image to generate temperature information. A user can preset a basis temperature. The central processing unit 40 is configured to receive the image and the thermal image, overlaps the image and the thermal image, calculates the temperature for each point of the thermal image and compares the calculated temperature with the basis temperature. The display unit 50 is connected to the central processing unit 40. The central processing unit 40 transmits the value of the temperature to the display unit 50 to display the value of the temperature exceeding the basis temperature. In this embodiment, the display unit 50 is a transparent display device. A user can see a real scene through the display unit 50. The temperature value is shown on display device 50 and located in a position where the temperature occurs in the real scene to be viewed by the user.

In addition, the wearable device 100 of the invention further includes a control board 60 through which the image and the thermal image are transmitted to the central processing unit 40. The control board 60 drives the image capturing unit 20 and the thermal sensing device 32.

The wearable device 100 of the invention further includes a power source 80 connected to the central processing unit 40. In this embodiment, the power source 80 is a battery. In another embodiment, the wearable device 100 of the invention further includes a power control board 90 coupled to the central processing unit 40. An external power source provides power for the wearable device 100 or charges the power source 80 through the power control board 90.

The wearable device 100 of the invention further includes a wireless transceiver 110 connected to the central processing unit 40. The central processing unit 40 transmits the value of the temperature to a control system through the wireless transceiver 110.

Figure 2:
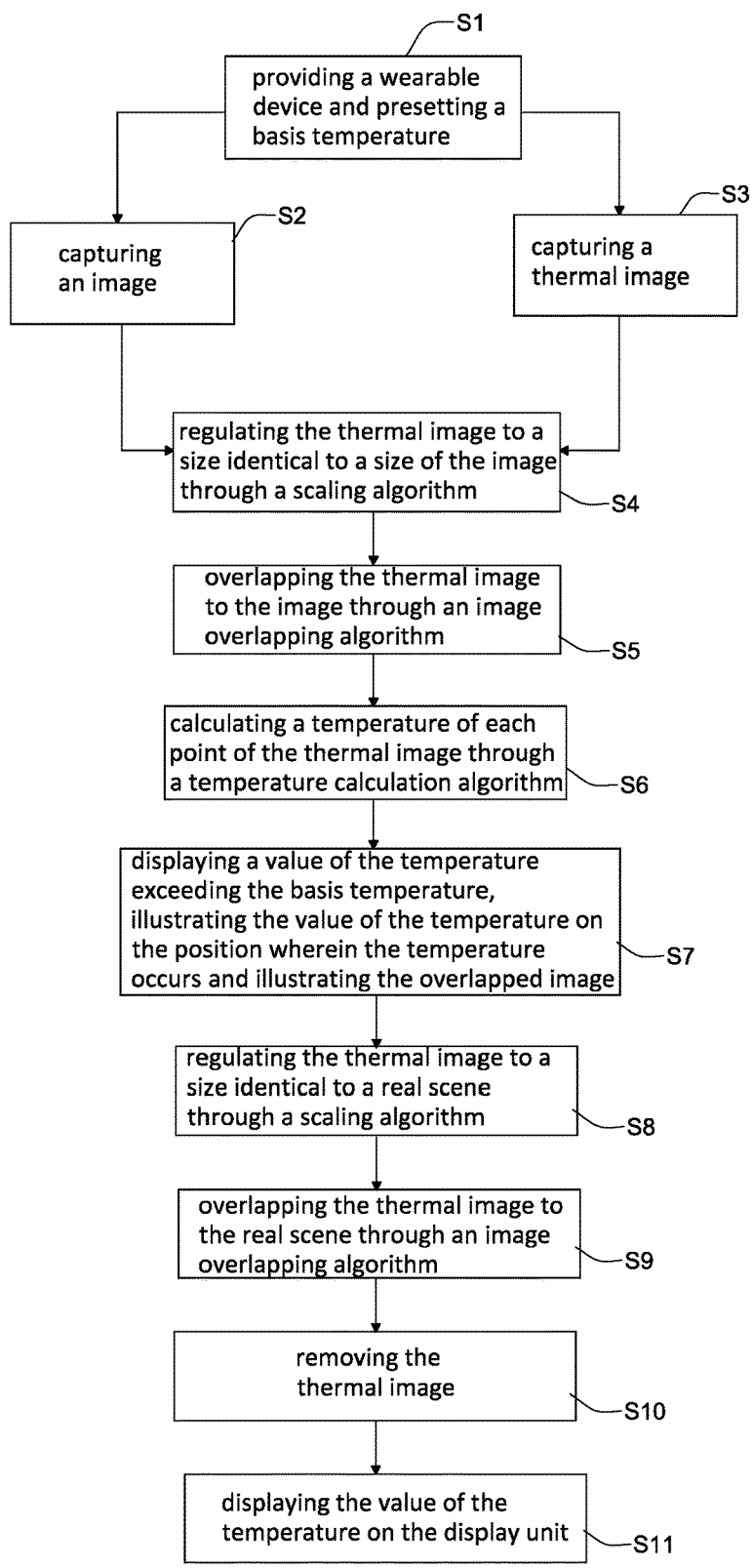
FIG. 2 is a flow chart of a method for displaying an object temperature of the invention.

Referring to FIG. 2, a method for displaying an object temperature of the invention is disclosed. In a step S1, a wearable device is provided. The wearable device includes an image capturing device, a thermal sensing device and a display unit, and a basis temperature can be preset by a user in the wearable device 100. The procedure enters a step S2. In the step S2, an image is captured through the image capturing device. The procedure enters a step S3. In the step S3, a thermal image is captured through the thermal sensing device. The procedure enters a step S4. In the step S4, the thermal image is regulated to a size identical to a size of the image through a scaling algorithm. The procedure enters a step S5. In the step S5, the thermal image is overlapped to the image through an image overlapping algorithm. The procedure enters a step S6. In the step S6, a value of the temperature in the thermal image is calculated through a temperature calculation algorithm. The procedure enters a step S7. In the step S7, the value of the temperature is compared with the basis temperature and the value of the temperature exceeding the basis temperature is illustrated on the position where the temperature occurs. The procedure enters a step S8. In the step S8, the thermal image is regulated to a size identical to a real scene through a scaling algorithm. The procedure enters a step S9. In the step S9, the thermal image is overlapped to the real scene through an image overlapping algorithm. The procedure enters a step S10. In the step S10, the thermal image is removed, but the value of the temperature and the real scene are remained. The procedure enters a step S11. In the step S11, the value of the temperature is displayed on the display unit.

A temperature of a thermal image is measured and displayed in a real time through the wearable device 100 of the invention. The wearable device 100 of the invention can be applied to quarantine, fire accident preventing or industry.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A wearable device configured to display a temperature of an object, comprising:
   a camera configured to receive external light to form an image;
   an image capturing unit configured to capture the image;
   a thermal camera configured to receive external light to generate a thermal image;
   a thermal sensing device configured to receive the thermal image to generate temperature information;
   a central processing unit configured to receive the image and the thermal image, overlap the image and the thermal image, calculate a value of a temperature for each point in the thermal image and compare the value of the temperature with a basis temperature; and
   a display unit connected to the central processing unit, wherein the central processing unit transmits the value of the temperature exceeding the basis temperature to the display unit to display the value of the temperature on a position where the temperature occurs.

2. The wearable device as claimed in claim 1, further comprising a control board through which the image and the thermal image are transmitted to the central processing unit.

3. The wearable device as claimed in claim 1, further comprising a power source coupled to the central processing unit.

4. The wearable device as claimed in claim 1, further comprising a power control board through which an external power source is coupled to the central processing unit.

5. The wearable device as claimed in claim 1, wherein the display unit comprises a transparent display device.

6. The wearable device as claimed in claim 1, further comprising a wireless transceiver connected to the central processing unit, wherein the wireless transceiver transmits the image and the value of the temperature to a control system.

7. The wearable device as claimed in claim 1, wherein the basis temperature is preset.

* * * * *